United States Patent [19]

Trivedi

[11] Patent Number: 5,116,848
[45] Date of Patent: May 26, 1992

[54] N-(((2,6-DISUBSTITUTED)PHENYL)-N-DIARYLALKYL)UREAS AS ANTIHYPERLIPIDEMIC AND ANTIATHEROSCLEROTIC AGENTS

[75] Inventor: Bharat K. Trivedi, Farmington Hills, Mich.

[73] Assignee: Warner-Lambert Company, Morris Plains, N.J.

[21] Appl. No.: 176,079

[22] Filed: Mar. 30, 1988

[51] Int. Cl.$^5$ .................. C07C 275/34; C07C 275/28; A61K 31/17

[52] U.S. Cl. .................. 514/332; 514/336; 514/342; 514/345; 514/353; 514/357; 514/444; 514/445; 514/447; 514/438; 514/585; 514/586; 514/587; 514/596; 514/598; 514/824; 564/27; 564/28; 564/29; 564/26; 564/48; 564/52; 546/261; 546/265; 546/284; 546/291

[58] Field of Search ............ 564/26, 28, 48, 52, 564/27, 29; 546/265, 284, 331, 332, 261, 291, 297, 300, 306; 549/59, 66, 62, 63, 65; 514/332, 336, 357, 444, 438, 585, 587, 596, 598, 342, 346, 353, 445, 447, 438

[56] References Cited

U.S. PATENT DOCUMENTS

| | | | |
|---|---|---|---|
| 2,911,393 | 11/1959 | Brooks et al. | 564/26 X |
| 3,028,391 | 4/1962 | Rorig | 546/331 |
| 4,387,105 | 6/1983 | DeVries et al. | 424/322 |
| 4,387,106 | 6/1983 | DeVries et al. | 424/322 |
| 4,397,868 | 8/1983 | DeVries | 564/48 X |
| 4,410,697 | 10/1983 | Torok et al. | 564/48 X |
| 4,473,579 | 9/1984 | DeVries et al. | 514/596 X |
| 4,623,662 | 11/1986 | DeVries | 574/596 |

FOREIGN PATENT DOCUMENTS 1461806 2/1975 United Kingdom ............... 546/331

Primary Examiner—Carolyn Elmore
Attorney, Agent, or Firm—Ruth H. Newtson

[57] ABSTRACT

Certain N-2,6-dialkyl- or N-2,6-dialkoxphenyl-N'-diarylalkylurea compounds are potent inhibitors of the enzyme acyl CoA:cholesterol acyltransferase (ACAT), and are thus useful agents for the treatment of hypercholesterolemia or atherosclerosis with urea and thiourea compounds.

9 Claims, No Drawings

N-(((2,6-DISUBSTITUTED)PHENYL)-N-DIARYLALKYL)UREAS AS ANTIHYPERLIPIDEMIC AND ANTIATHEROSCLEROTIC AGENTS

BACKGROUND OF THE INVENTION

This invention relates to chemical compounds having pharmacological activity, to pharmaceutical compositions which include these compounds, and to a pharmaceutical method of treatment. More particularly, this invention concerns certain substituted urea and thiourea compounds which inhibit the enzyme acyl-coenzyme A:cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

U.S. Pat. No. 4,387,105 to DeVries, et al. discloses a method of treating atherosclerosis employing certain dialkylurea and dialkylthiourea compounds.

U.S. Pat. No. 4,387,106 to DeVries, et al. discloses a method of treating atherosclerosis using certain N-phenyl- or N-[substituted(phenyl)]-N',N'-dialkylurea and thiourea compounds.

U.S. Pat. No. 4,387,106 to DeVries, et al. discloses methods for treating atherosclerosis using certain trisubstituted N-[substituted(phenyl)]-N',N'-diarylalkyl urea and thiourea compounds.

U.S. Pat. No. 4,397,868 to DeVries, et al. discloses methods for treating atherosclerosis using certain trisubstituted urea compounds.

U.S. Pat. No. 4,473,579 to DeVries, et al. discloses certain tetrasubstituted urea compounds and their use as agents for treating atherosclerosis.

U.S. Pat. No. 4,623,662 to DeVries discloses a method of reducing arterial wall deposits of cholesterol employing certain trisubstituted urea and thiourea compounds.

SUMMARY OF THE INVENTION

The present invention provides a class of compounds with ACAT inhibitory activity having the structure

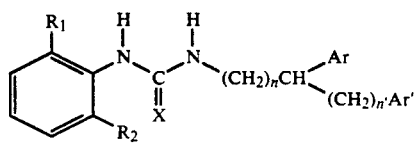

where n is zero or an integer of from one to four, n' is zero or an integer of from one to three, and X is oxygen or sulfur. $R_1$ and $R_2$ are independently selected from alkyl or alkoxy of from one to six carbon atoms. Ar and Ar' are independently selected from phenyl, 1- or 2-naphthyl, 2- or 3-thienyl, or 2-, 3-, or 4-pyridinyl any of which may be unsubstituted or substituted by alkyl of from one to six carbon atoms, hydroxy, alkoxy of from one to six carbon atoms, fluorine, chlorine, bromine, nitro, benzyloxy, trifluoromethyl, or $-NR_5R_6$ in which $R_5$ and $R_6$ are independently hydrogen or alkyl of from one to six carbon atoms, or NH-acetyl with the proviso that when Ar and Ar' are both not phenyl or substituted phenyl, n is one and n' is zero.

DETAILED DESCRIPTION

The compounds of the present invention form a class of substituted ureas and thioureas having potent activity as inhibitors of the enzyme acyl CoA:cholesterol acyltransferase (ACAT) and thus are useful as agents for the treatment of hypercholesterolemia and atherosclerosis.

In the compounds of the present invention, the first nitrogen atom of the urea moiety is monosubstituted by a phenyl group which is substituted in the 2- and 6-positions by alkyl or alkoxy groups. Preferred compounds of this invention are the 2,6-dialkylsubstituted compounds, with 2,6-bis(1-methylethyl) being the most preferred.

The second nitrogen atom of the urea moiety of compounds of this invention is monosubstituted with a diarylalkyl group in which the aryl groups may be unsubstituted phenyl, naphthyl, thienyl, or pyridinyl groups or phenyl, naphthyl, thienyl, or pyridinyl groups substituted with alkyl of from one to six carbon atoms, alkoxy of from one to six carbon atoms, fluorine, chlorine, bromine, trifluoromethyl, benzyloxy, or $NR_5R_6$ wherein $R_5$ is hydrogen and $R_6$ is acetyl or where $R_5$ and $R_6$ are independently selected from hydrogen, alkyl of from one to four carbon atoms, or benzyl.

In those cases where Ar and Ar' are both selected from groups other than phenyl or substituted phenyl as defined above, the preferred values of n and n' are one and zero, respectively.

Examples of compounds contemplated as falling within the scope of the invention are the following:

N-(2,6-Diethylphenyl)-N'-(1,2-diphenylethyl)urea;
N-(2,6-Diethylphenyl)-N'-(diphenylmethyl)urea;
N-(2,6-Diethylphenyl)-N'-(2,2-diphenylethyl)urea;
N-[2,6-bis(1-methylethyl)phenyl]-N'-(2,2-diphenylethyl)urea;
N-[2,6-bis(1-methylethyl)phenyl]-N'-(diphenylmethyl)urea;
N-[2,6-bis(1-methylethyl)phenyl]-N'-(1,2-diphenylethyl)urea;

By the term "alkyl" as used throughout this specification and the appended claims is meant a branched or unbranched hydrocarbon grouping derived from a saturated hydrocarbon of from one to six carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

By the term "alkoxy" is meant an alkyl group, as defined above, attached to the parent molecular moiety through an oxygen atom.

In those instances where the compounds of the present invention bear a basic nitrogen atom, the compounds are capable of forming acid addition salts. These acid addition salts are also contemplated as falling within the scope of this invention.

While the acid addition salts may vary from the free base form of the compounds in certain properties such as melting point and solubility, they are considered equivalent to the free base forms for the purposes of this invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts. (See, for example, Stephen N. Berge, et al. *J. Pharm. Sciences*, 66:1-19 (1977).

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired by methods known in the art as, for example, the separation of stereoisomers in chiral chromatographic columns.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

The compounds of the present invention are prepared by reacting the appropriately 2,6-disubstituted isocyanate or thioisocyanate with the desired amine.

The reaction is generally carried out in a polar aprotic organic solvent such as ethyl acetate, at any temperature between room temperature and the boiling point of the solvent, with room temperature being preferred.

The reaction is allowed to proceed until analysis of the mixture by a means such as chromatography indicates that the reaction is substantially complete. Reaction times may vary between about two hours to about 24 hours, depending upon the particular reagents and reaction temperature employed. The starting isocyanate and thioisocyanate compounds are known or commercially available or, if not previously known, are prepared by methods well known in the art from the corresponding amine compounds. The starting diarylamine compounds are also known or easily synthesized from commercially available starting materials by methods well known in the art.

As shown by the data presented below in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

In Vitro Tests

The ability of representative compounds of the present invention to inhibit ACAT was measured using an in vitro test more fully described in Field, F. J. and Salone, R. G., *Biochemica et Biophysica* 712:557-570 (1982). The test assesses the ability of a test compound to inhibit the acylation of cholesterol by oleic acid by measuring the amount of radio-labeled cholesterol oleate formed from radiolabeled oleic acid in a tissue preparation containing rabbit intestinal microsomes.

The data appear in Table 1 where they are expressed as $IC_{50}$ values; i.e. the concentration of test compound required to inhibit 50% expression of the enzyme.

TABLE 1

| Compound of Example | $IC_{50}$ ($\mu$M) |
| --- | --- |
| 1 | 0.093 |
| 2 | 0.080 |
| 3 | 0.091 |
| 4 | 0.024 |
| 5 | 0.045 |

In Vivo Tests

In one in vivo screen, designated PCC, male Sprague-Dawley rats (approximately 200 g body weight) are randomly divided into groups and provided ad libidum a regular chow diet (Purina No. 5002, Ralston Purina Co., 711 West Fuesser Road, Mascoutah, Ill., 62224, USA), supplemented with 5.5% peanut oil, 1.5% cholesterol, and 0.3%-0.5% cholic acid, together with 0.05% of the test drug which is admixed into the diet. After one week the animals are etherized and a blood sample is taken from the heart and mixed with 0.14% ethylenediamine tetraacetic acid (EDTA) to measure the total cholesterol. The results of this trial for representative compounds of the present invention appear in Table 2.

TABLE 2

| Compound of Example | Blood Cholesterol (mg/dl) | % Change |
|---|---|---|
| 1 | 147 (207)* | −29 |
| 2 | 127 (223) | −43 |
| 3 | 105 (223) | −53 |
| 4 | 95 (197) | −52 |

In therapeutic use as agents for treating hypercholesterolemia or atherosclerosis, the compounds utilized in the pharmaceutical method of this invention are administered to the patient at dosage levels of from 250 to 1000 mg per day. For a normal human adult of approximately 70 kg of body weight, this translates into a dosage of from 5 to 20 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following preparative examples are provided to enable one skilled in the art to practice the invention, and are illustrative thereof. They are not to be read as limiting the scope of the invention as it is defined by the appended claims.

EXAMPLE 1

Preparation of N-(2,6-Diethylphenyl)-N'-(1,2-diphenylethyl)urea

To a solution of 1,2-diphenylethylamine (1.0 g, 0.005 mol) in 50 ml of ethyl acetate, there was added 0.88 g (0.005 mol) of 2,6-diethylphenyl isocyante. The resulting mixture was stirred at room temperature for 20 hours.

The precipitated solid was collected by filtration, washed with ethyl acetate, and dried to yield 1.72 g of N-(2,6-diethylphenyl)-N'-(1,2-diphenylethyl)urea.

Analysis for $C_{25}H_{28}N_2O$: Calc.: C=80.61%, H=7.57%, N=7.52%; Found: C=80.49%, H=7.66%, N=7.47%.

EXAMPLE 2

Preparation of N-(2,6-Diethylphenyl)-N'-(diphenyl methyl)urea

The title compound, mp 238°–240° C., was prepared from 2,6-diethylphenyl isocyante and diphenylmethylamine according to the method of Example 1.

Analysis for $C_{24}H_{26}N_2O$: Calc.: C=80.41%, H=7.30%, N=7.81%; Found: C=80.14%, H=7.45%, N=7.87%.

EXAMPLE 3

Preparation of N-(2,6-Diethylphenyl)-N'-(2,2-diphenylethyl)urea

The title compound, mp 200°–201° C., was prepared from 2,6-diethylphenyl isocyanate and 2,2-diphenylethylamine according to the method of Example 1.

Analysis for $C_{25}H_{28}N_2O$: Calc.: C=80.61%, H=7.57%, N=7.52%; Found: C=80.75%, H=7.66%, N=7.61%.

EXAMPLE 4

Preparation of N-[2,6-bis(1-methylethyl)phenyl]-N'-(2,2-diphenylethyl)urea

The title compound, mp 175°–176° C., was prepared from 2,6-bis(1-methylethyl)phenyl isocyanate and 2,2-diphenylethylamine according to the method of Example 1.

Analysis for $C_{27}H_{32}N_2O$: Calc.: C=80.96%, H=8.05%, N=6.99%; Found: C=80.58%, H=8.01%, N=6.79%.

EXAMPLE 5

Preparation of N-[2,6-bis(1-methylethyl)phenyl]-N'-(diphenylmethyl)urea

The title compound, mp 245°–246° C., was prepared from N-2,6-bis(1-methylethyl)phenyl isocyanate and diphenylmethylamine according to the general method of Example 1.

Analysis for $C_{26}H_{30}N_2O$: Calc.: C=80.79%, H=7.82%, N=7.24%; Found: C=80.80%, H=7.78%, N=7.34%.

EXAMPLE 6

Preparation of N-[2,6-bis(1-methylethyl)phenyl]-N'-(1,2-diphenylethyl)urea

The title compound, mp 219°–221° C., was prepared from N-2,6-bis(1-methylethyl)phenyl isocyanate and 1,2-diphenylethylamine according to the general method of Example 1.

Analysis for $C_{27}H_{32}N_2O$: Calc.: C=80.96%, H=8.05%, N=6.99%; Found: C=80.97%, H=7.97%, N=7.15%.

I claim:

1. A compound having the structural formula

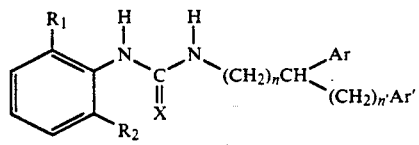

wherein $R_1$ and $R_2$ are independently selected from alkyl of from one to six carbon atoms, alkoxy of from one to six carbon atoms;

n is zero or an integer of from one to four;

n' is zero or an integer of from one to three;

X is oxygen or sulfur;

Ar and Ar' are independently unsubstituted phenyl, 1- or 2-naphthyl, 2- or 3-thienyl, or 2-, 3-, or 4-pyridinyl; or phenyl, 1- or 2-naphthyl, 2- or 3-thienyl, or 2-, 3-, or 4-pyridinyl substituted with alkyl of from one to six carbon atoms,
  hydroxy,
  alkoxy of from one to six carbon atoms,
  fluorine,
  chlorine,
  bromine,
  nitro,
  benzyloxy,
  trifluoromethyl, or
  —$NR_5R_6$ in which $R_5$ and $R_6$ are independently hydrogen or alkyl of from one to six carbon atoms; or NH-acetyl with the proviso that when Ar and Ar' are both not phenyl or substituted phenyl, n is one and n' is zero; or a pharmaceutically acceptable salt thereof.

2. A compound as defined by claim 1 having the name N-(2,6-diethylphenyl)-N'-(1,2-diphenylethyl)urea.

3. A compound as defined by claim 1 having the name N-(2,6-diethylphenyl)-N'-(diphenylmethyl)urea.

4. A compound as defined by claim 1 having the name N-(2,6-Diethylphenyl)-N'-(2,2-diphenylethyl)urea.

5. A compound as defined by claim 1 having the name N-[2,6-bis(1-methylethyl)phenyl]-N'-(2,2-diphenylethyl)urea.

6. A compound as defined by claim 1 having the name N-[2,6-bis(1-methylethyl)phenyl)-N'-(diphenylmethyl)urea.

7. A compound as defined by claim 1 having the name N-[2,6-bis(1-methylethyl)phenyl)-N'-(1,2-diphenylethyl)urea.

8. A pharmaceutical composition for treating hypercholesterolemia or atherosclerosis comprising an ACAT-inhibitory effective amount of a compound as defined by claim 1 in combination with a pharmaceutically acceptable carrier.

9. A method of treating hypercholesterolemia or atherosclerosis comprising administering to a mammal in need of such treatment an ACAT-inhibitory effective amount of a compound as defined by claim 1.

* * * * *